US006368813B1

(12) United States Patent
Reznik et al.

(10) Patent No.: US 6,368,813 B1
(45) Date of Patent: Apr. 9, 2002

(54) MULTIFLAVOR STREPTAVIDIN

(75) Inventors: Gabriel O. Reznik, Boston; Takeshi Sano, Needham; Sandor Vajda, Medfield; Cassandra Smith, Boston, all of MA (US); Charles Cantor, Del Mar, CA (US)

(73) Assignee: The Trustees of Boston University, Boston, MA (US)

( * ) Notice: Subject to any disclaimer, the term of this patent is extended or adjusted under 35 U.S.C. 154(b) by 0 days.

(21) Appl. No.: 09/381,430

(22) PCT Filed: Mar. 13, 1998

(86) PCT No.: PCT/US98/04931

§ 371 Date: Mar. 23, 2000

§ 102(e) Date: Mar. 23, 2000

(87) PCT Pub. No.: WO98/40396

PCT Pub. Date: Sep. 17, 1998

Related U.S. Application Data

(60) Provisional application No. 60/040,771, filed on Mar. 14, 1997, now abandoned.

(51) Int. Cl.[7] .................. G01N 33/53; C07K 14/00; C07H 21/04
(52) U.S. Cl. .................. 435/7.5; 435/7.1; 435/69.1; 530/350; 530/300; 536/23.7; 536/23.1
(58) Field of Search .................. 536/23.1, 23.7; 530/350, 300, 324; 435/69.1, 7.1, 7.5, 440

(56) References Cited

U.S. PATENT DOCUMENTS

| 5,624,896 A | 4/1997 | Axworthy et al. |
| 5,630,996 A | 5/1997 | Reno et al. |
| 5,648,274 A | 7/1997 | Chandler |
| 6,103,493 A | * 8/2000 | Skerra et al. ............ 435/69.1 |

FOREIGN PATENT DOCUMENTS

| WO | WO 96/24606 | 8/1996 |
| WO | WO 97/00329 | 1/1997 |

OTHER PUBLICATIONS

Chilkoti et al., "Site–directed mutagenesis studies of the high affinity streptavidin–biotin complex: Contributions of tryptophan residues 79, 108 and 120.", Feb. 1995, Proc. Natl. Acad. Sci. USA., vol. 92, pp. 1754–1758.*
Chilkoti, et al., *J. Am. Chem. Soc.*, 117:10622–10628 (1995).
Moy, et al., *Science*, 266:257–259 (1994).
Rusckowski et al., *Nucl. Med. Commun.*, 16:38–46 (1995).

* cited by examiner

*Primary Examiner*—Karen Cochrane Carlson
*Assistant Examiner*—Rita Mitra
(74) *Attorney, Agent, or Firm*—Ronald I. Eisenstein

(57) ABSTRACT

Compounds and methods are described for producing streptavidin mutants with changed affinities. In particular, modifications to the sequence of the natural streptavidin gene is described to create amino acid substitutions resulting in greater affinity for biotin substitutes than for biotin.

21 Claims, No Drawings

SEQUENCE LISTING

<160> NUMBER OF SEQ ID NOS: 2

<210> SEQ ID NO 1
<211> LENGTH: 638
<212> TYPE: DNA

<213> ORGANISM: Streptomyces avidinii

<400> SEQUENCE: 1

| | | | | | |
|---|---|---|---|---|---|
| ccctccgtcc | ccgccgggca | acaactaggg | agtattttc | gtgtctcaca | tgcgcaagat | 60 |
| cgtcgttgca | gccatcgccg | tttccctgac | cacggtctcg | attacggcca | gcgcttcggc | 120 |
| agacccctcc | aaggactcga | aggcccaggt | ctcggccgcc | gaggccggca | tcaccggcac | 180 |
| ctggtacaac | cagctcggct | cgaccttcat | cgtgaccgcg | ggcgccgacg | gcgccctgac | 240 |
| cggaacctac | gagtcggccg | tcggcaacgc | cgagagccgc | tacgtcctga | ccggtcgtta | 300 |
| cgacagcgcc | ccggccaccg | acggcagcgg | caccgccctc | ggttggacgg | tggcctggaa | 360 |
| gaataactac | cgcaacgccc | actccgcgac | cacgtggagc | ggccagtacg | tcggcggcgc | 420 |
| cgaggcgagg | atcaacaccc | agtggctgct | gacctccggc | accaccgagg | ccaacgcctg | 480 |
| gaagtccacg | ctggtcggcc | acgacacctt | caccaaggtg | aagccgtccg | ccgcctccat | 540 |
| cgacgcggcg | aagaaggccg | gcgtcaacaa | cggcaacccg | ctcgacgccg | ttcagcagta | 600 |
| gtcgcgtccc | ggcaccggcg | ggtgccggga | cctcggcc | | | 638 |

<210> SEQ ID NO 2
<211> LENGTH: 159
<212> TYPE: PRT
<213> ORGANISM: Streptomyces avidinii

<400> SEQUENCE: 2

Asp Pro Ser Lys Asp Ser Lys Ala Gln Val Ser Ala Ala Glu Ala Gly
1               5                   10                  15

Ile Thr Gly Thr Trp Tyr Asn Gln Leu Gly Ser Thr Phe Ile Val Thr
            20                  25                  30

Ala Gly Ala Asp Gly Ala Leu Thr Gly Thr Tyr Glu Ser Ala Val Gly
        35                  40                  45

Asn Ala Glu Ser Arg Tyr Val Leu Thr Gly Arg Tyr Asp Ser Ala Pro
    50                  55                  60

Ala Thr Asp Gly Ser Gly Thr Ala Leu Gly Trp Thr Val Ala Trp Lys
65                  70                  75                  80

Asn Asn Tyr Arg Asn Ala His Ser Ala Thr Thr Trp Ser Gly Gln Tyr
                85                  90                  95

Val Gly Gly Ala Glu Ala Arg Ile Asn Thr Gln Trp Leu Leu Thr Ser
            100                 105                 110

Gly Thr Thr Glu Ala Asn Ala Trp Lys Ser Thr Leu Val Gly His Asp
        115                 120                 125

Thr Phe Thr Lys Val Lys Pro Ser Ala Ala Ser Ile Asp Ala Ala Lys
    130                 135                 140

Lys Ala Gly Val Asn Asn Gly Asn Pro Leu Asp Ala Val Gln Gln
145                 150                 155

MULTIFLAVOR STREPTAVIDIN

This patent application claims priority to PCT/US98/04931, filed Mar. 13, 1998, which claims priority benefit of U.S. Provisional Application Serial No. 60/040,771, filed Mar. 14, 1997, abandoned.

This invention was made with government support under U.S. Department of Energy Grant No. DE-FG02-93ER61656. The Government of the United States of America has certain rights in the invention.

FIELD OF THE INVENTION

The present invention relates to compounds and methods, and in particular, modified streptavidin having affinity for biotin substitutes.

BACKGROUND

The biological sciences have been employed since early times by mankind to modify living organisms or their constitutive elements for a variety of purposes, such as the production of foods and therapeutic agents. However, only during the last fifty years there has been progress at the genetic level to gain a much better understanding of the essential component of living systems. This has led to the understanding that nucleic acids, in the form of DNA and RNA, store and distribute genetic information that determines the sequences of amino acids that characterize proteins; proteins contribute to the structure of an organism and execute most of the tasks required for its function and that even proteins form part of the mechanism by which they are synthesized (e.g. chaperones); polysaccharides, linear and branched polymer of sugars, provide structural elements, store energy, and when combined with peptides or proteins play an important role in cellular recognition; lipids, which include molecules such as fatty acids, phospholipids, and cholesterol, serve as energy sources and are the most important components of the membrane structures that organize and compartmentalize cellular function.

However, proteins are the biological macromolecules with the greatest functional diversity. Proteins catalyze most reactions that occur in living cells, or serve as inhibitors of enzymatic reactions. They transport oxygen, electrons and energy to specific regions in the cell. Other proteins protect living organisms by recognizing and binding to foreign substances. There are also proteins that have a structural function such as collagen, the main constituent of connective tissue fibrils and bones, or have functional roles such as actin or myosin, which are involved in muscle dynamics.

Most proteins biological function is derived from interactions with other molecules such as ligands, hormones, coenzymes or other biological compounds. As a result of this action, there can be important structural changes in both the protein and the other molecule. These conformational changes, in many occasions, are essential for activity; but in other cases they are not as relevant. In hormone-receptor binding, for example, structural changes are fundamental to the transmission of information. Consequently, elucidation of reactive, and non-reactive interactions that are possible between a protein and a ligand is essential for the correct understanding of the molecular mechanisms that govern protein recognition by another molecule.

One of the most remarkable non-reactive protein-ligand interaction involves a 60-kDa tetrameric protein that originates from the actinobacterium *Streptomyces avidinii* termed streptavidin [Chaiet and Wolf, "The Properties of Streptavidin, a biotin-binding protein produced by Streptomycetes," *Arch. Biochem. Biophys.*106:1–5 (1964)] and the small organic molecule biotin. The binding of biotin by streptavidin is accompanied by one of the largest decreases in free energy observed for a non-covalent interaction in aqueous solution (Ka~1015 M-1)[Green, "Avidin," *Adv. Protein Chem.* 29:85–133 (1975)].

The high association constant of the streptavidin-biotin complex, which is four to six orders of magnitude higher than most antigen-antibody interactions, has many useful applications in the biological sciences. The streptavidin-biotin system has been exploited to devise widely applicable tools in microbiology [Suzuki et al., "Chemiluminescent enzyme-linked immunoassay for reverse transcriptase, illustrated by detection of HIV reverse transcriptase," *Anal. Biochem.* 210:277–28 (1993)], biochemistry [Katz, "Binding to protein targets of peptidic leads discovered by phage display: crystal structures of streptavidin-bound linear and cyclic peptide ligand containing the HPQ sequence," *Biochem.* 34:15421–15429 (1995)] and biotechnology [Bayer and Wilchek, "The use of the avidin-biotin complex as a tool in molecular biology," *Methods Biochem. Anal.* 26:1–45 (1980); Fuccillo, "Application of the Avidin-Biotin Technique in Microbiology," *Biotechniques* 3:494–501 (1985); Buckland, "Strong signals from streptavidin-biotin," *Nature* 320:557–558 (1986)], as well as in the medical sciences, for example, for the localization and separation of antigens [Zaar, "Light and electron microscopic localization of D-aspartate oxidase in peroxisomes of bovine kidney and liver: an immunocytochemical study," *J. Histochem. and Cytochem.* 44:1013–1019 (1996)], immunotherapy [Bodey et al., "Immunophenotypically varied cell subpopulations in primary and metastatic human melanomas. Monoclonal antibodies for diagnosis, detection of neoplastic progression and receptor directed immunotherapy," *Antican. Res.* 16:517–531 (1996)], immunoassay development [Heuer et al., "Development of a sensitive peptide-based immunoassay: application to detection of the Jun and Fos oncoproteins," *Biochem.* 35:9069–9075 (1996)], Hybridization studies [Nilsson et al., "Real-time monitoring of DNA manipulations using biosensor technology," *Anal. Biochem.* 224:400–408 (1995)], tumor localization [Puy et al., "Immunocytochemical detection of androgen receptor in human temporal cortex characterization and application of polyclonal androgen receptor antibodies in frozen and paraffin-embedded tissues," *J. Steriod Biochem. and Mol. Biol.* 55:197–209 (1995); Sung et al., "Streptavidin distribution in metastatic tumors pretargeted with a biotinylated monoclonal antibody: theoretical and experimental pharmacokinetics," *Cancer Res.* 54:2166–2175 (1994)] and delivery of radionuclides to cancerous cells [van Osdol et al., "A distributed pharmacokinetic model of two-step imaging and treatment protocols: application to streptavidin-conjugated monoclonal antibodies and radiolabeled biotin," *J. Nucl. Med.* 34:1552–1564 (1993); Kalofonos et al., "Imaging of tumor in patients with Indium-111-labeled biotin and streptavidin conjugated antibodies: preliminary communication," *J. Nucl. Med.* 31:1791–1796 (1990); Pimm et al., "Iodine-131 and indium-111 labeled avidin and streptavidin for pretargeted immunoscintigraphy with biotinylated anti-tumor monoclonal antibody," *Nucl. Med. Commun.* 9:931–941 (1988)].

SUMMARY OF THE INVENTION

The present invention relates to compounds and methods, and in particular, modified streptavidin having affinity for biotin substitutes. The compounds and methods of the present invention are particularly useful where levels of endogenous biotin are present in the system, precluding the use of the standard biotin-avidin approach. In addition, it is contemplated that the streptavidin-biotin system can be used as a model to test if the contacts that exist between a protein and a ligand can serve as the starting point to genetically engineer the protein to develop a high specificity for another ligand. Amino acid substitutions are designed to reduce the affinity for the original ligand and obtain a much higher affinity for the substitute molecule. The guiding consideration for re-designing the biotin-binding site of streptavidin was to significantly reduce biotin-binding by minimizing amino acids substitutions in residues making hydrogen bonds with biotin to preserve this contacts for other biotin-like molecules. To test this, the biotin derivatives 2-iminobiotin and diaminobiotin were selected as biotin substitutes (although other substitutes are possible, including compounds that are not biotin derivatives).

In one embodiment, the present invention contemplates a nucleic acid sequence encoding a streptavidin mutant having a higher affinity for a biotin substitute than for biotin. An illustrative streptavidin mutant has a higher affinity for 2-iminobiotin than for biotin. In a specific embodiment, the sequence encodes a streptavidin mutant consisting of amino acids 16 to 133 of the 159-amino acid natural streptavidin, wherein said sequence comprises one or more codon substitutions such that said mutant comprises one or more amino acid substitutions. While a variety of substitutions are possible (including combinations of substitutions), in one embodiment the codon for Asn at position 23 of said 159-amino acid natural streptavidin is substituted with a codon for Ala; in another embodiment, the codon for Ser at position 27 of said 159-amino acid natural streptavidin is substituted with a codon for Glu; in still another embodiment, the codon for Ser at position 27 of said 159-amino acid natural streptavidin is substituted with a codon for Asp.

In a preferred embodiment, the present invention contemplates a nucleic acid sequence encoding a streptavidin mutant consisting of amino acids 16 to 133 of the 159-amino acid natural streptavidin, wherein said sequence comprises one or more codon substitutions such that said mutant comprises one or more amino acid substitutions and has a higher affinity for a biotin substitute than for biotin.

The present invention also contemplates the resulting protein and uses for the protein. In one embodiment, the present invention contemplates a streptavidin mutant having a higher affinity for a biotin substitute than for biotin. In a specific embodiment, the mutant consists of amino acids 16 to 133 of the 159-amino acid natural streptavidin, wherein said mutant comprises one or more amino acid substitutions (including but not limited to substitutions wherein i) Asn at position 23 of said 159-amino acid natural streptavidin is substituted with Ala; ii) Ser at position 27 of said 159-amino acid natural streptavidin is substituted with Glu; and iii) Ser at position 27 of said 159-amino acid natural streptavidin is substituted with Asp.

In a specific embodiment, the present invention contemplates a streptavidin mutant consisting of amino acids 16 to 133 of the 159-amino acid natural streptavidin, wherein said mutant comprises one or more amino acid substitutions and has a higher affinity for 2-iminobiotin than for biotin.

The strategy is contemplated to be useful to develop a receptor for a molecule without a known receptor when phage-display methodologies cannot be employed, such as in the case of a multi-chain protein, for the discovery of new drugs and diagnostic reagents, or in applications were the use of one molecule is well-suited for a project but the other one is not. The design, construction, and analysis of two streptavidin constructs are discussed below.

DESCRIPTION OF THE INVENTION

A. The Streptavidin-Biotin Complex

Biotin is small organic molecule present in all living cells. Its chemical name is cis-hexahydro-2-oxo-1 H-thieno[3,4] imidazole-4-pentanoic acid. Biotin, also known as vitamin H, has a molecule weight of 244.31 and the molecular composition C10H16N2O3S (FIG. 1) [Savage et al., "Components of Avidin-Biotin Technology," in *Avidin-Biotin Chemistry: A Handbook,* Pierce Chemical Co. (1992)].

Biotin functions as a coenzyme for carboxylating enzymes that catalyze the incorporation of carbon dioxide into substrates [Wood and Barden, "Biotin Enzymes," *Annu. Rev. Biochem.* 46:385–413 (1977)]. Examples of these carboxylases include pyruvate carboxylase, trans-carboxylase, acetyl-CoA carboxylase, and b-methylcrotonyl-CoA carboxylase.

This compound is a protein that has been isolated from culture filtrates of streptomycetes [Chaiet and Wolf, "The Properties of Streptavidin, a biotin-binding protein produced by Streptomycetes," *Arch. Biochem. Biophys.*106:1–5 (1964)]. Initial studies showed that this biomolecule is one of the contributing substances that make up the antibiotic MSD-235. Further research on this antibiotic [Taussig and Wolf, "Streptavidin. A substance with avidin-like properties produced by microorganisms," *Biochem. Biophys. Res. Commun.* 14:205–209 (1964)] revealed that its activity is inhibited by biotin, suggesting that this protein binds biotin. Since this biomolecule was isolated from the soil bacterium *Streptomyces avidinii,* and it has a remarkable similarity to chicken egg white avidin in its ligand-binding affinity, it has been named streptavidin. Avidin and streptavidin are approximately of the same size [Chaiet and Wolf, "The Properties of Streptavidin, a biotin-binding protein produced by Streptomycetes," *Arch. Biochem. Biophys.*106:1–5 (1964); Green, "Avidin," *Adv. Protein Chem.* 29:85–133 (1975)], tetrameric, and with a 33% identity in amino acid sequence [Argaraña et al., "Molecular cloning and nucleotide sequence of the streptavidin gene," *Nucl. Acid. Res.* 14:871–882 (1986); Pähler et al., "Characterization and crystallization of core streptavidin," *J. Biol. Chem.* 262:13933–13937 (1987)].

Tetrameric streptavidin has a molecular mass of approximately 60 kDa [Tausig and Wolf, "Streptavidin. A substance with avidin-like properties produced by microorganisms," *Biochem. Biophys. Res. Commun.* 14:205–209 (1964)], with each of its subunits encoded by the same gene [Green, "Avidin," *Adv. Protein Chem.* 29:85–133 (1975)]. Each streptavidin subunit is organized as eight-stranded, sequentially connected, antiparallel b-sheets, in a manner that the first and last b-sheets are adjacent and hydrogen bonded to one another [Hendrickson et al., "Crystal structure of core streptavidin determined from multiwavelength anomalous diffraction of synchrotron radiation," *Proc. Natl. Acad. Sci. USA* 86:2190–2194 (1989); Weber et al., "Structural origins of high-affinity biotin binding to streptavidin," *Science* 243:85–88 (1989)]. Pairs of streptavidin barrels are connected by hydrogen bonds to form symmetric dimers which are very stable due to the presence of complementary surfaces that allow extensive van der Waals interactions, hydrogen bonds, and electrostatic forces between subunits forming a dimer. The naturally occurring streptavidin tetramer is formed by interdigitating a pair of such dimers, with their dyad axes coincident, and is stabilizing by van der Waals and electrostatic forces across the dimer-dimer (weak) interface [Weber et al., "Structural origins of high-affinity biotin binding to streptavidin," Science 243:85–88 (1989)].

Each subunit of natural core streptavidin has molecular mass of 15 kDa; however, subunits undergo postsecretory degradation resulting in subunits with a molecular mass of approximately 14 kDa [Bayer et al., "Postsecretory modification of streptavidin," Biochem. J. 259:369–376 (1989)]. Streptavidin is proteolyzed, but not always completely, at both ends of the 159-residue gene product (SEQ ID NO: 2) to form a 125–127 residue core [Argaraña et al., "Molecular cloning and nucleotide sequence of the streptavidin gene," Nucl. Acid. Res. 14:871–882 (1986); Hendrickson et al., "Crystal structure of core streptavidin determined from multiwavelength anomalous diffraction of synchrotron radiation," Proc. Natl. Acad. Sci. USA 86:2190–2194 (1989); Sano et al., "Recombinant core streptavidins. A minimum-sized core streptavidin has enhanced structural stability and higher accessibility to biotinylated macromolecules," J. Biol. Chem. 270:28204–28209 (1989)]. The streptavidin gene used below codes for a core streptavidin consisting of only 118 amino acids and comprises amino acids 16 to 133 [Sano and Cantor, "Expression opf a cloned streptavidin gene in Escherichia coli," Proc. Natl. Acad. Sci. USA 87:142–146 (1990)] of the 159-amino acid natural streptavidin gene (SEQ ID NO:1). In this manner, the work was done with a single species of streptavidin molecules instead of proteolyzed streptavidins with variable length. However, the present invention contemplates that longer and shorter portions of the natural gene (and corresponding protein) can be used with the desired substitutions to alter affinity. Moreover, substitutions that do not change affinity may be made in addition to those substitutions (described below) which alter affinity.

B. The Biotin-binding Site of Streptavidin

The interaction between biotin and amino acids in the biotin-binding site of streptavidin takes place with residues exclusively of one subunit with the exception of Trp-120 which comes from the adjacent subunit [Chilkoti et al., "Site-directed mutagenesis studies of the high-affinity streptavidin-biotin complex: Contributions of tryptophan residues 79, 108, and 120," Proc. Natl. Acad. Sci. USA 92:1754–1758 (1995); Sano and Cantor, "Intersubunit contacts made by tryptophan 120 with biotin are essential for both strong biotin binding and biotin-induced tighter subunit association of streptavidin," Proc. Natl. Acad. Sci. USA 92:3180–3184 (1995)] across the dimer-dimer interface. Biotin is buried deeply inside the barrel with only the carboxyl oxygens and the ureido ring nitrogen protruding to the outside. Numerous hydrogen bonds and van der Waals interactions are involved in the binding of biotin to the aromatic and polar amino acids lining the streptavidin binding site. These include three hydrogen bonds to the carbonyl group, plus five additional hydrogen bonds to the ureido nitrogens, carboxyl group, and thiophan sulphur of biotin. In addition, four tryptophans are in contact with each biotin molecule [Hendrickson et al., "Crystal structure of core streptavidin determined from multiwavelength anomalous diffraction of synchrotron radiation," Proc. Natl. Acad. Sci. USA 86:2190–2194 (1989); Weber et al., "Structural origins of high-affinity biotin binding to streptavidin," Science 243:85–88 (1989)].

C. Materials and Methods

1. Construction of Expression Vectors

Expression vectors were constructed by using a bacteriophage M13mp18 derivative, mpSA-29, which codes for a core streptavidin consisting of amino acids 16 to 133, as a starting material. Mutations were introduced into the coding sequence for streptavidin by using an oligonucleotide-directed in vitro mutagenesis system (Amersham)[Sayers et al., "5'-3' exonucleases in phosphorothioate-based oligonucleotide-directed mutagenesis," Nucl. Acids. Res. 16:791–802 (1988)].

Two sets of mutations, each involving two codon substitutions, were made separately on the streptavidin gene to severely weaken biotin-binding and attain a stronger affinity for 2-iminobiotin or diaminobiotin: Asn-23 (AAC) for Ala (GCT) and Ser-27 (TCG) for Asp (GAC); Asn-23 (AAC) for Ala (GCT) and Ser-27 (TCG) for Glu (GAA). The coding sequence containing the desired mutations was cloned into the Nde I site of plasmid pET-3a under the control of the f10 promoter [Studier et al., "Use of T7 RNA polymerase to direct expression of cloned genes," Methods Enzymol. 185:60–89 (1990); Studier and Moffatt, "Use of bacteriophage T7 RNA polymerase to direct selective high-level expression of cloned genes," J. Mol. Biol. 189:113–130 (1986)]. The resulting expression vector pTSA-A23D27 encodes the streptavidin mutant Stv-A23D27, in which Asn-23 is replaced by Ala and Ser-27 is replaced by Asp. The second expression vector pTSA-A23E27 encodes the streptavidin mutant Stv-A23E27, in which Asn-23 is replaced by Ala and Ser-27 is replaced by Glu.

2. Expression and Purification of Streptavidin Mutants

Expression of the streptavidin mutants Stv-A23D27 and Stv-A23E27 was carried out as previously described [Sano and Cantor, "Expression opf a cloned streptavidin gene in Escherichia coli," Proc. Natl. Acad. Sci. USA 87:142–146 (1990)] by using E. coli strain BL21(DE3)(pLysE) [Studier et al., "Use of T7 RNA polymerase to direct expression of cloned genes," Methods Enzymol. 185:60–89 (1990)] carrying an expression vector. Stv-A23E27 required the addition of 10 mM urea during the renaturation step to increase the protein yield. Stv-A23D27, and Stv-A23E27 renatured fractions were applied separately to a diaminobiotin-agarose (Sigma) column. Stv-A23D27 and Stv-A23E27 were bound to the immobilized ligand in the presence of 0.02% Tween, 0.02% sodium azide, 0.5 M sodium chloride, 0.2 M ammonium acetate (pH 6.0). Prior to elution, the column was washed to remove unbound proteins with 0.02% Tween, 10 mM urea, 0.5 M sodium chloride, 0.2 M ammonium acetate (pH 6.0). Stv-A23D27 bound proteins were eluted with 0.02% Tween, 10 mM urea, 50 mM sodium carbonate (pH 10.0). Elution of Stv-A23E27 was done with 10 mM urea, 0.02% Tween, 50 mM CHES (pH 9.0). After purification, Stv-A23D27 and Stv-A23E27 were dialyzed separately against water and stored at 4° C. 3. Preparation of 2-Iminobiotin-$^{14}$C-Glycine and 2-Imnobiotin-$^{3}$H-Glycine NHS-iminobiotin, dissolved in dimethylformamide (DMF), was combined in a 50:1 molar ratio with either $^{14}$C-glycine (98 mCi/mmol and 104 mCi/mmol; Amersham) or $^{3}$H-glycine (18.6 Ci/mmol; Amersham) dissolved in 50 mM sodium borate (pH 8.0). The final concentration of DMF was 10%. The reaction mixture was incubated for 1 hr. Radiolabeled iminobiotin was purified from unreacted glycine, NHS-iminobiotin and iminobiotin by FPLC using a reversed-phase column (RPC HR5/5; Pharmacia; Piscataway). The binding buffer was 100 mM potassium phosphate (pH 2.5). The iminobiotin-glycine product was obtained by washing the column with 20 bed volumes of the binding buffer. Fractions containing radiolabeled material (2×2.1 ml) were reloaded into reversed-phase column with water as the binding buffer. The radiolabeled iminobiotin-glycine material was lyophilized and resuspended in 150 mM sodium chloride, 50 mM Hepes (pH 7.5). 4. Preparation of 2-Iminobiotin-$^{14}$C-Glycine Cystamine, dissolved in 0.5 sodium chloride and 0.2 M sodium bicarbonate (pH 8.3) reacted with NHS-sepharose (1 ml Hi-Trap column, 10 mmol/ml; Pharmacia) with an estimated ratio of amines to NHS groups of 100. The reaction mixture was incubated for 30 minutes at room temperature (~23° C.) then packed in a column. Free cystamine was removed by extensively washing the column with 0.5 M sodium chloride, 0.2 M sodium bicarbonate (pH 8.3). Sepharose-cystamine molecules were then resuspended in 7.5 ml of 50 MM sodium borate (pH 8.0) and one tenth of this volume was combined with 19 mg of NHS-iminobiotin (25.3 mg/ml in DMF; Pierce or Sigma) to crosslink NHS-iminobiotin with the available amino group of cystamine on sepharose-cystamine. The reaction mixture was incubated for 1 hr at room temperature and then packed in a column. Free iminobiotin was removed by extensively washing the column with 0.5 sodium chloride, 1 M urea, 50 mM sodium borate (pH 8.0). The column was equilibrated with 0.5 M Tris-HCl (pH 8.2) and then incubated for 1 hr at room temperature with a 10 molar excess of dithiothreitol over estimated immobilized cystamine to cleave the disulfide bond present in cystamine. The released 2-iminobiotin-cysteamine molecules were carboxymethylated with $^{14}$C-iodoacetamide (Dupont) in an estimated 1:1 ratio for 3 hours at room temperature. The carboxymethylation reaction was terminated by the addition of 2-mercaptoethanol. Labeled iminobiotin molecules were purified using streptavidin-agarose (Sigma)[Hofmann et al., "Imminobiotin affinity columns and their application to retrieval of streptavidin," Proc. Natl. Acad. Sci. USA 77:4666–4668 (1990)]. Using the same protocol, iminobiotin-cysteamine-acetamide molecules were prepared using unlabeled iodoacetamide.

5. Determination of Association Constants

The association constant between Stv-A23D27 and biotin, and Stv-A23E27 and biotin was measured by incubating Stv-A23D27, and Stv-A23E27 separately at a final concentration of 23.8 mM and 5.96 mM, respectively with various amounts of biotin (Sigma). Streptavidin to biotin molar ratios ranged from 1 to 10. Approximately, 0.3% of the biotin used was D-[8, 9-$^3$H]biotin (47 Ci/mmol; Amersham).

The association constant between Stv-A23D27 and 2-iminobiotin-$^{14}$C-glycine, and Stv-A23E27 and 2-iminobiotin-$^{14}$C-glycine was measured by incubating Stv-A23D27, and Stv-A23E27 separately at the same final concentration of 1.38 mM with various amounts of 2-iminobiotin-$^{14}$C-glycine. Streptavidin to 2-iminobiotin-glycine molar ratios ranged from 1 to 10 for both streptavidins.

The affinity constant between Stv-A23D27 and 2-iminobiotin, and Stv-A23E27 and 2-iminobiotin was estimated by competition with 2-iminobiotin-$^{14}$C-glycine. Stv-A23D27, and Stv-A23E27 were incubated separately at the same final concentration of 1.38 mM with a 7:1 molar excess of 2-iminobiotin-$^{14}$C-glycine over available binding sites. 2-Iminobiotin molar ratios to streptavidin range from 1–12 for both constructs.

The affinity constant between Stv-A23D27 and diaminobiotin, and Stv-A23E27 and diaminobiotin was estimated by competition with 2-iminobiotin-$^{14}$C-glycine. Stv-A23D27, and Stv-A23E27 were incubated separately at the same final concentration of 2.3 mM with a 7:1 molar excess of 2-iminobiotin-$^{14}$C-glycine over available binding sites. Diaminobiotin to Stv-A23D27 molar ratios ranged from 1–50, whereas diaminobiotin to Stv-A23E27 molar ratios ranged between 1–200.

All mixtures were incubated between 18–24 hr to reach equilibrium at 25° C. All reactions were carried out in 200 ml of 150 mM NaCl, 50 mM Hepes (pH 7.5). Total radiolabeled ligand concentration was determined by collecting 9.5 ml of the total reaction volume and measuring the amount of radiation present by liquid scintillation counting. Free ligands were separated from streptavidin-ligand complexes by filtration using Ultrafree-MC centrifugal filter units (molecular mass cutoff, 10 kDa; Millipore), and quantitated (9.5 ml) by liquid scintillation counting. To minimize disruption of the equilibrium conditions, approximately 14 ml of the remaining 190.5 ml were passed through the filtering device.

6. Other Methods

Protein concentrations were quantitated by measuring their absorbance at 280 using the extinction coefficient 3.55. SDS-PAGE analysis [Sambrook et al., in *Molecular Cloning: A Laboratory Manual,* 2nd Ed. Cold Spring Harbor Laboratory Press, Plainview, N.Y. (1989)] was carried out using 15% polyacrylamide gels. Proteins were stained with Coomassie Brilliant Blue or by silver staining (BioRad). Ligand-binding ability was determined by gel filtration chromatography [Laemmli, "Cleavage of structural proteins during the assembly of the head of bacteriophage T4," *Nature* 227:680–685 (1970)] using PD-10 columns (Pharmacia) or by using Ultrafree-MC centrifugal filter units (molecular mass cutoff, 10 kDa; millipore) with iminobiotin-$^{14}$C-glycine or D-[carbonyl-$^{14}$C]biotin [Wei, "Assay of Avidin," *Methods Enzymol.* 18A:424–427 (1970)].

D. Redesign of the Streptavidin Binding-Biotin Site: Streptavidin Analogs With a Higher Affinity for Other Small Molecules than for Biotin Streptavidin binds biotin with an extremely high affinity due to a very large network of contacts between these two molecules, as described earlier. Such a network provides a very interesting starting point to investigate if it is possible to adapt the biotin-binding site of streptavidin as a receptor for another molecule by taking advantage of the large number of residues that are involved in biotin-binding.

The streptavidin biotin-binding site was redesigned to develop a higher affinity for the biotin derivative 2-iminobiotin than for biotin. This compound was chosen for its similar structure as biotin and the likelihood of preserving some of the same contacts between biotin and streptavidin after modifications introduced in the biotin-binding site (however, substitutes that are less similar to biotin are contemplated). This biotin derivative has identical structure as biotin with the exception that the ureido group of biotin is replaced by a guanidino group. Two streptavidin constructs, each having two amino acid substitutions, were designed by site-directed mutagenesis of Ser-27 to Asp or Glu, in addition to Asn-23 replaced by Ala. These streptavidin constructs were characterized to see the effect of these modifications on biotin and 2-iminobiotin and learn if it is possible to provide the biotin-binding site of streptavidin with specificity for a biotin derivative. These mutants were designed based on the theoretical considerations described below.

1. Theoretical Design of Recombinant Streptavidins

The successful design and construction of streptavidin constructs that are able to bind a biotin derivative with a higher association constant than biotin was obtained by combining computer simulations data and experimental work based on: the published crystallographic structure of streptavidin [Hendrickson et al., "Crystal structure of core streptavidin determined from multiwavelength anomalous diffraction of synchrotron radiation," Proc. Natl. Acad. Sci. USA 86:2190–2194 (1989); Weber et al., "Structural origins of high-affinity biotin binding to streptavidin," Science 243:85–88 (1989)], existing data between a protein similar to streptavidin named avidin and biotin-like molecules, and data from a molecular dynamics/free energy perturbation approach [Miyamoto and Kollman, "Absolute and Relative binding free energy calculations of the interaction of biotin and its analogs with streptavidin using molecular dynamics/free energy perturbation approaches," Proteins: Structure, Function, and Genetics 16:226–245 (1993)] carried out on the streptavidin-biotin system.

The computational approach involved a molecular dynamics/free energy perturbation simulation for the design of streptavidin constructs. Initial calculations were carried out on the streptavidin-biotin complex to test the methodology and refine the parameters used in the simulation so it would agree with prior experimental data on this system [Green, "Avidin," Adv. Protein Chem. 29:85–133 (1975)]. To predict the free energy of streptavidin-biotin complex formation to within an error of 2 kcal/mol, it was necessary to introduce dessolvation effects to account for the streptavidin-water, biotin-water as well as (streptavidin-biotin)-water interactions. The information derived from these simulations provided clues to design recombinant streptavidins and allowed for the making of a few constructs to achieve the desired goal. The computational approach used to obtain these streptavidins is discussed below along with the current methods that are used in computer simulations to study protein-ligand interactions.

2. Computational Strategies for Protein Design and Study of Protein-ligand Interactions Computational approaches to protein design fall into two general categories: those that do not use information on the structure of a binding site and structure-based approaches that do use this information to analyze ligand binding. In the first approach, researchers utilize large databases containing ligands in order to find a good match or matches for the binding site(s) of a protein. In this approach, there is no prior knowledge of the properties of the binding site(s) of the protein studied. Although this procedure may not yield the best possible ligand(s), it provides an initial candidate that can be further improved using a structure-activity technique. This second approach, that involves quantitative structure-activity relationship (QSAR) techniques provide the best approach to rational drug design. Traditional QSAR methods attempt to correlate protein function, which has yet to be determined, with atom type and whole molecular properties such as charge and hydrophobicity present in the protein binding site [Jackson, "Update on computer-aided drug design," Curr. Opin. Biotech. 6:646–651 (1995)].

The method used to obtain streptavidin constructs with a higher association constant for 2-iminobiotin than for biotin falls under QSAR techniques since the structure and properties of 2-iminobiotin were used to rationally redesign the biotin-binding site of streptavidin. A somewhat similar approach is the one used by the computer program COMPASS that has been developed to deduce the properties of a binding site from the three dimensional shape and surface properties of a series of ligands interacting with this site [Jain et al., "COMPASS: predicting biological activities from molecular surface properties. Performance comparisons on a steroid benchmark," J. Med. Chem. 37:2315–2327 (1994); Jain et al., "COMPASS: a shape-based machine learning tool for drug design," J. Comput. Aided. Mol. Des. 8:635–652 (1994)]. Another program, called PROLIGAND [Waszkowycz et al., "PROLIGAND: an approach to de novo molecular design. 2. Design of novel molecules from molecular field analysis models and pharmachores," J. Med. Chem. 37:3994–4002 (1994)], characterizes ligands as well as binding sites with respect to charged and hydrophobic regions, as well as ligand groups as either hydrogen bond donors or acceptors; in addition, with all this information, the program is also able to search a library of fragments to construct new ligands with the required properties to achieve high affinity at a site.

The approach to find a biotin derivative that has a higher affinity for streptavidin than biotin was done by selecting a ligand and then modifying streptavidin residues to achieve the objective. A different approach might have involved the disruption of contacts involved in biotin binding followed by the technique of affinity fingerprinting [Kauvar et al., "Predicting ligand binding to proteins by affinity fingerprinting," Chem. Biol. 2:107–118 (1995)] to design a ligand that would bind to the biotin-binding site with a higher affinity than biotin. Affinity fingerprinting is a method based on observations that most ligands bind to a large number of proteins to a greater or lesser extent. Therefore, this method suggests that it is possible to use a large number of ligands to discover the characteristics that define the fingerprint of the binding site of a protein and then build such a ligand.

The interaction energy of streptavidin-ligand complexes was calculated using a docking algorithm. This algorithm seek to predict the structure and binding free energy of a ligand-receptor complex given only their structural information [Jones and Willett, "Docking small-molecule ligands into active sites," Curr. Opin. Biotech. 6:652–656 (1995)]. A complete model of ligand-protein docking requires both ligand and protein flexibility, variable positioning of the ligand and full protein-water-ligand interactions. Unfortunately, a detailed treatment of protein-ligand interactions is not feasible due to computational constraints. To diminish the complexity of the problem, simplified models have been attempted that consider both proteins and ligands rigid. In general, comparison between theoretical predictions and experimental results indicate that accurate docking results cannot be obtained unless the starting protein and ligand conformations are not far from their active conformation (the bound conformation of the target protein and its ligand). Because that active conformation is not necessarily the same as in the crystal or in solution, it is very difficult to determine the active conformations of flexible ligand molecules without elaborate experiments.

The apparent limitations in the rigid-body docking methods has led to the formation of less restrictive approaches [Mizutani et al., "Rational automatic search method for stable docking models of protein and ligand," J. Mol. Biol. 243:310–326 (1994); DesJarlais et al, "Docking flexible ligands to macromolecular receptors by molecular shape," J. Med. Chem. 29:2149–2153 (1986)]. Docking of ligands to proteins requires an algorithm that allows some conformational flexibility of both protein and ligand. This methodology must assume that the protein is rigid during early stages of the docking procedure, but then it allows side chain and ligand flexibility to ensure that there is a good fit and the energy minimum achieved is a global-energy minimum. To obtain a protein-ligand conformation with such requirement, several docking models are searched interactively and energy minimized by molecular mechanics calculation, and the model with the lowest energy among them is considered the global-minimum energy structure. The computer simulations followed this method. Streptavidin side chains were flexible; however, the protein backbone remained rigid to minimize the computational task.

There are different approaches used in the search for an energy minimum and in the criteria used to choose a particular conformation among many possible conformations. In Kuntz's algorithm [Kuntz et al., "A geometric approach to macromolecule-ligand interactions," *J. Mol. Biol.* 161:269–288 (1982)] both the ligand and the macromolecular surface are represented by sets of spheres and the best minimized structures are the ones that have the best surface complementarity. The many resulting orientations are then scored by an approximate van der Waals energy function that includes electrostatic effects between the spheres. This scoring function takes no account of the dessolvation that may occur during the formation of the protein-ligand complex.

The system by Miller [Miler et al., "FLOG: a system to select 'quasi-flexible' ligands complementary to a receptor of known three-dimensional structure," *J. Comput. Aided. Mol. Des.* 8:153–174 (1994)] uses a modified version of Kuntz's algorithm to search a database in which the conformational space of each flexible ligand is represented by up to 25 distinct low-energy conformations, that covers most of the ligand's possible conformational space, and uses a similar scoring procedure. Another modified version of the Kuntz's algorithm introduces ligand flexibility by dividing the ligand structure into several rigid fragments, which are docked separately and later rejoined into the whole ligand in different conformations.

Bacon and Moult [Bacon and Moult, "Docking by least-squares fitting of molecular surface patterns," *J. Mol. Biol.* 225:849–858 (1992)] fit molecular surfaces to each other to provide a new solution to the problem of docking a ligand into the active site of a protein molecule. The procedure constructs patterns of points on the surfaces [Fischer et al., "A geometry-based suite of molecular docking processes," *J. Mol. Biol.* 248:459–477 (1995)] and superimposes them upon each other using a least-squares best-fit algorithm. This brings the surfaces into contact and provides a direct measure of their local complementarity. The search over the ligand surface produces a large number of dockings, of which a small fraction having the best complementarity and the least steric hindrance are evaluated for electrostatic interaction energy.

The algorithm of Smellie [Smellie et al., "Fast drug-receptor mapping by site-directed distances: a novel method of predicting new pharmacological leads," *J. Chem. Inform. Comp. Sci.* 31:386–392 (1991)] determines the binding modes between a protein and a flexible ligand only considering hydrogen bonds made between atoms in both molecules. This method does not produce actual docking models but rather possible binding modes between two molecules because docking algorithms require embedded ligand molecules in a protein cavity.

An alternative docking method utilizes Brownian dynamics to provide motion to two types of reactants that begin in close proximity to one another. This algorithm represents both ligands and proteins by spheres, where the protein active site region is defined by a surface area lying within 10° of a line running from the center to the surface of a sphere, or by considering an active site which is recessed from the spherical surface of a protein and lies within a cone that defines an active site channel [Allison et al., "Extended Brownian dynamics of diffusion controlled reactions," *J. Chem. Phys.* 83:2894–2899 (1985)].

Many of the above procedures utilize Montecarlo [Guida et al., "Probing the conformational space available to inhibitors in the thermolysin active site using montecarlo/energy minimization techniques," *J. Comp. Chem.* 13:214–228 (1992)] or Molecular Dynamics [Banci et al., "Molecular dynamics characterization of the active cavity of carboxypeptidase A and some of its inhibitors adducts," *Proteins: Structure, Function, and Genetics* 13:288–305 (1992)] simulations to obtain low energy conformations between proteins and ligands. In the first procedure, atomic motions are selected randomly, and the resulting changes are accepted with a Boltzmann probability distribution as follows: if $\exp(-DE/kt)$ is larger than a random number between zero and one, then the new conformation is accepted; otherwise, the change is rejected and a new random configuration is selected. In molecular dynamics simulations, molecules move in response to force fields that account for van der Waals and electrostatic energies as well as rotational and elastic bond energies, that take into account their torsional flexibility and elasticity, both of which are represented by spring-like energy formulas.

An alternative computational method for the motion of flexible molecules into protein binding sites uses a genetic algorithm. In this approach, several initial configurations evolve through the process of selection, breeding, and mutation [Judson et al., "A genetic algorithm based method for docking flexible molecules," *J. Molec. Struc.* 308:191–206 (1993)]. For selection purposes, many initial configurations are subdivided in smaller groups called niches. Each population of configurations has all of its variables such as bond lengths, torsional angles, stored in gray-coded binary representation. Low energy configurations which lead to new generations are obtained using three procedures: by promoting the configurations with the lowest energy within each niche, by selecting low energy configurations among those resulting from random mutation of bits, and by exchanging information between configurations that have low energies. This selection process is repeated until there is convergence in energy among the best fitted configurations of each niche. These configurations represent the best fit between a ligand and a protein binding site.

The redesign of the streptavidin biotin-binding site utilized a docking algorithm that allow partial flexibility of streptavidin and full flexibility of ligands. The description below illustrates more clearly the strategy used to adapt the biotin-binding site for a biotin derivative.

3. Computational Redesign of the Streptavidin Biotin-binding Site

The vast information regarding the streptavidin biotin-binding site and its affinity for the small molecule biotin was used to make a complete and careful computational redesign of the site by allowing the inclusion of dessolvation effects, which become important when considering a flexible ligand and are usually excluded when dealing with macromolecules. Among this information, the known three-dimensional crystallographic structure of the streptavidin-biotin complex [Hendrickson et al., "Crystal structure of core streptavidin determined from multiwavelength anomalous diffraction of synchrotron radiation," *Proc. Natl. Acad. Sci. USA* 86:2190–2194 (1989); Weber et al., "Structural origins of high-affinity biotin binding to streptavidin," *Science* 243:85–88 (1989)], together with existing molecular dynamics/free energy perturbation approaches [Miyamoto and Kollman, "Absolute and Relative binding free energy calculations of the interaction of biotin and its analogs with streptavidin using molecular dynamics/free energy perturbation approaches," *Proteins: Structure, Function, and Genetics* 16:226–245 (1993); Vajda et al., "Effect of conformational flexibility and solvation on receptor-ligand binding free energies," *Biochem.* 33:13977–13988 (1994)] was particularly useful. The amino acid substitutions required to weaken biotin-binding and simultaneously strengthen streptavidin's affinity for a biotin analog was analyzed using the theory detailed below prior to the actual construction of these streptavidins by genetic engineering.

The search for such streptavidins assumed that the streptavidin backbone remains rigid, despite it has been observed in the crystallographic analysis of streptavidin that a loop changes conformation upon binding [Hendrickson et al., "Crystal structure of core streptavidin determined from multiwavelength anomalous diffraction of synchrotron radiation," *Proc. Natl. Acad. Sci. USA* 86:2190–2194 (1989); Weber et al., "Structural origins of high-affinity biotin binding to streptavidin," *Science* 243:85–88 (1989)]. This was assumed throughout the simulations to minimize the computational effort. Such a simplification does not affect the outcome of energy perturbations calculations, which showed negligible energy differences between rigid and flexible backbone models. However, protein side chains as well as the ligands considered were allowed flexibility. To reproduce the biomolecules behavior in liquid environment, water solvation effects were included in the simulations.

The criteria used to select the amino acid substitutions on the streptavidin gene is described below. The subscripts s, 1, and w label streptavidin, ligand and water, respectively, and the superscripts f and b denote quantities prior and subsequent to complex formation (i.e., free and bound states). The energy is the free state is given by $$E^f = E_s^f + E_l^f + E_w^f + E_{s-w}^f + E_{l-w}^f \quad (EQ\ 1)$$

where the last two terms refer to the separate interaction of streptavidin and ligands with water, respectively. The energy in the bound state is given by $$E^b = E_s^b + E_l^b + E_w^b + E_{s-l}^b + E_{(s-l)-w}^b \quad (EQ\ 2)$$

The energy change upon binding can be obtained by calculating the difference between EQ 2 and EQ 1.

$$= \Delta E_s + \Delta E_l + E_{s-l}^b + [E_{(s-l)-w} - E_{s-w}^f - E_{l-w}^f + \quad (EQ\ 3)$$

where the last term DEw accounts for changes in the self-energy of water. Each of the terms in EQ 3 is a sum over energies of all atoms in the complex, with each term accounting for electrostatic and van der Waals energies. The first two terms in EQ 3 can be neglected because the conformational energy change of both streptavidin and biotin is very small upon formation of the complex. Another simplification that reduces computational work is the fact that protein-ligand and protein-solvent interfaces are well-packed to the extent that changes in the van der Waals component of DEs-1 and DE1-w and DEs-w are very small, so that it is only necessary to consider electrostatic forces for these terms [Adamson, in *Physical Chemistry of Surfaces*, Wiley, N.Y. (1976); Novotny et al., "On the attribution of binding energy in antigen-antibody complexes McPC603, D1.3, and HyHEL-5," *Biochem.* 28:4735–4749 (1989)]. To calculate the Gibbs free energy (EQ 4) it is necessary to calculate the entropic contribution, namely T(Sb-Sf), where T is temperature and S, entropy, and the subscripts refer to streptavidin with and without biotin.

$$\Delta G = \Delta H - T \Delta S \quad (EQ\ 4)$$

The terms that contribute to the entropy are DStr, the rotational and translational entropy change; DSsc, the conformational entropy change of the side chains that become buried upon formation of the streptavidin-complex; and DSh, the hydrophobic entropy change. Therefore, EQ 4 becomes $$\Delta G = E_{s-l}^{el} + \Delta G_h - T\Delta S_{sc} - T\Delta S_{tr} \quad (EQ\ 5)$$

The electrostatic energy is given by a Coulombic potential controlled by a switching function that turns electrostatic interactions off for distances greater than or equal to 17 Å. The dielectric constant is replaced by 4r, a distance dependent dielectric, which is a linear approximation between the dielectric constant of water which equals 78, and the dielectric constant of well packed protein atoms taken to be approximately 2.

The translational/rotational contributions to the entropy are taken as a constant factor to a good approximation independent of the complex [Erickson, "Co-operativity in protein-protein association. The structure and stability of the actin filament," *J. Mol. Biol.* 206:465–474 (1989)]. In all of the simulations, this approximation does not have any serious consequences because we are interested in changes in free energy difference between streptavidin-biotin-analog complexes and streptavidin-biotin, namely $$\Delta\Delta G = \Delta G_{biotin} - \Delta G_{biotinlikemolecule} \quad (EQ\ 6)$$

On the other hand, careful calculations were done to determine both conformational and hydrophobic contributions to the entropy because they depend on the chemical nature of the interacting molecules. Contributions to hydrophobic free energy are based on a procedure [Eisenberg and McLachlan, "Solvation energy in protein folding and binding," *Nature* 319:199–203 (1986)] that calculates the free energy of transferring a molecule from a hydrophobic to a hydrophillic media (octanol to water). This is done by calculating a solvent-exposed surface area for each of the following five types of atoms charged (N— or O—), polar uncharged (N/O or S), and apolar (C) for each of the 20 amino acid side chain types. Then, the change in the hydrophobic energy can be readily calculated according to $$\Delta G_h = \Delta G_h^{s-l} - \Delta G_h^l - \Delta G_h^s \quad (EQ\ 7)$$

The change in the conformational entropy was obtained by monitoring the side chains of the proteins and ligand that become buried (not exposed to water) as a result of the complex formation. Entropic changes were obtained by scaling the amount of side chain that lost contact with water according to DS=a DSmax, where a takes into account the fraction of side chain that became buried upon complex formation. It was assumed that all side chain conformational entropy of an amino acid was lost when 60% or more of the its solvent-accessible area becomes buried as a result of complex formation. Smax is evaluated using the relationship in EQ 8, with the pij values, the probability of side chain type j being in conformational state i, according to data observed in distributions of exposed side-chains in proteins with the known X-ray structures [Pickett and Sternberg, "Empirical scale of side-chain conformational entropy in protein folding," *J. Mol. Biol.* 231:825–839 (1993)].

$$S_{max} = -R_i \Sigma p_{ij} \ln(p_{ij}) \quad \text{(EQ 8)}$$

E. Results and Discussion

1. Design of Stv-A23D27 and Stv-A23E27

The large number of hydrogen bonds and numerous van der Waals interactions that exist between streptavidin and biotin [Hendrickson et al., "Crystal structure of core streptavidin determined from multiwavelength anomalous diffraction of synchrotron radiation," *Proc. Natl. Acad. Sci. USA* 86:2190–2194 (1989); Weber et al., "Structural origins of high-affinity biotin binding to streptavidin," *Science* 243:85–88 (1989)] present an attractive starting point to investigate if it is possible to adapt the biotin-binding site of streptavidin as a receptor for another molecule by taking advantage of the large number of residues that are involved in biotin-binding. This would be accomplished by introducing amino acid substitutions in streptavidin in order to shift its specificity for biotin to that for the biotin derivative 2-iminobiotin.

The novel aspect of this problem is that modifications in the streptavidin biotin-binding site should both decrease the affinity for biotin while providing a higher affinity for a biotin derivative. The design was constrained to molecules able to retain the majority of the contacts and shape complementarity that is present between streptavidin and biotin in order to preserve a strong binding. This considerations simplified the design and provided strong guidelines leading to the desired products.

Although initially we considered replacing one of the amino acids in the streptavidin binding site to produce steric hindrance between that amino acid and biotin to prevent biotin binding, this idea was promptly discarded because such a modification would have likely produced a major change in the resulting three-dimensional structure of the protein and made very difficult the search for a small molecule with a very high affinity for the redesigned streptavidin biotin-binding site. Instead, analysis of published data between the protein avidin, which is remarkably similar to streptavidin, and a wide variety of biotin derivatives [Green, "Avidin," *Adv. Protein Chem.* 29:85–133 (1975); Green, "Thermodynamics of the binding of biotin and some analogs by avidin," *Biochem. J.* 101:774–780 (1966)] provided a detailed picture of the effects of stepwise modifications of the biotin structure on the ability to bind to the streptavidin biotin-binding site. These results indicate that amino acid substitutions on residues that interact with the biotin ureido oxygen would diminish the high affinity between streptavidin and biotin. The three-dimensional structure of the streptavidin-biotin complex reveals that side chains of Asn-23, Ser-27, and Tyr-43 make hydrogen bonds with the ureido oxygen [Hendrickson et al., "Crystal structure of core streptavidin determined from multiwavelength anomalous diffraction of synchrotron radiation," *Proc. Natl. Acad. Sci. USA* 86:2190–2194 (1989); Weber et al., "Structural origins of high-affinity biotin binding to streptavidin," *Science* 243:85–88 (1989].

The molecular dynamics/free energy perturbation approach carried out on the streptavidin-biotin complex using partial atomic charges data obtained earlier [Miyamoto and Kollman, "Absolute and Relative binding free energy calculations of the interaction of biotin and its analogs with streptavidin using molecular dynamics/free energy perturbation approaches," *Proteins: Structure, Function, and Genetics* 16:226–245 (1993)] also suggests that mutations that destabilize the three hydrogen bonds with the ureido oxygen would weaken biotin-binding ability. Since the estimated theoretical partial atomic charge on the ureido oxygen is −0.65 e [Miyamoto and Kollman, "Absolute and Relative binding free energy calculations of the interaction of biotin and its analogs with streptavidin using molecular dynamics/free energy perturbation approaches," *Proteins: Structure, Function, and Genetics* 16:226–245 (1993)] and the carbonyl group of biotin is pH insensitive, the introduction of basic amino acids in the biotin-binding site of streptavidin, such as Asp or Glu (pKCOOH 1.88 and 2.19, respectively) [Lehninger et al. in *Principles of Biochemistry, pp.* 113, 2nd Ed. Worth Publishers, Inc. NY (1996)], might cause sufficient electrostatic repulsion between the carboxyl groups of these amino acids and the biotin ureido oxygen to lower the affinity between streptavidin and biotin. This led to the design of two streptavidins constructs that replace the residue Ser-27 with either Asp or Glu. Ser-27 was preferred over Asn-23 and Tyr-43 due to its proximity to the biotin ureido group. The introduction of such mutations suggested that good substitutes to replace biotin are biotin derivatives that possess a positively charged group at the location of the ureido group of biotin, such as 2-iminobiotin and diaminobiotin. These molecules have similar structure to biotin and might be able to favorably interact with the carboxyl group at residue 27. Further computer simulations indicated it was necessary to eliminate a possible hydrogen bond between biotin and Asn-23 by replacing this amino acid with Ala. Thus, this led to the construction of two streptavidin constructs Stv-A23D27, and Stv-A23E27, having the substitutions Ser-27 to Asp and Asn-23 to Ala, and Ser-27 to Glu and Asn-23 to Ala, respectively.

2. Expression and purification of streptavidin mutants

Stv-A23D27 and Stv-A23E27 were expressed efficiently in *Escherichia coli* using the T7 expression system. Both constructs were purified to homogeneity by a simple procedure that included diaminobiotin affinity chromatography. Unlike Stv-A23D27 that forms a stable tetrameric molecule with yields of ~900 mg/100 ml of culture, Stv-A23E27 has an approximate five-fold lower renaturation ability.

We attempted to improve Stv-A23D27 renaturation efficiency by increasing salt concentration and varying pH conditions (pH 4–6). Yields moderately increased to 100–200 mg/100 ml of culture when 10 mM urea was added in the renaturation step, as judged by SDS-PAGE by measuring the amount tetramer present in the renatured soluble fraction. Stv-A23E27 yields more than doubled with the addition of 2-iminobiotin in the renaturation step; however, this protein could not be recovered using diaminobiotin-agarose, as judged by SDS-PAGE as described above, probably because of the strong binding between the construct and 2-iminobiotin. The presence of diaminobiotin in the renaturation step of Stv-A23E27 also improved protein yields; however, purification of diaminobiotin-streptavidin constructs with 2-iminobiotin-agarose (Sigma) yielded no detectable amount of immobilized protein, also as judged by SDS-PAGE.

The purification procedure for Stv-A23D27 and Stv-A23E27 was developed by incubating approximately 3 mg of each protein in separate containers with 2-iminobiotin-agarose and diaminobiotin-agarose in a pH range from 2 to 11. Diaminobiotin-agarose bound Stv-A23D27, and Stv-A23E27 in a pH range from 4 to 9, and from 5 to 8, respectively, as judged by SDS-PAGE. The compound 2-iminobiotin-agarose bound Stv-A23D27, and Stv-A23E27 in a pH range from 7 to 11, and from 5 to 11, respectively. Then, elution conditions were determined. Proteins bound to diaminobiotin-agarose were incubated in solutions in a pH range from 2 to 5 and in a pH range from 8 to 11 to promote protein release; proteins bound to 2-iminobiotin-agarose were incubated in solutions in a pH range from 1.5 to 4. Affinity chromatography with diaminobiotin-agarose yielded streptavidins purified to homogeneity. Elution from 2-iminobiotin-agarose could only be achieved under denaturing conditions.

3. Preparation of radiolabeled diaminobiotin and radiolabeled 2-Iminobiotin

The radiolabeling of biotin derivatives, such as 2-iminobiotin or diaminobiotin, required the covalent linkage of at least one of these biotin derivatives to a radiolabeled molecule to measure the association constant between the newly designed streptavidins and these derivatives by competition assays. Experiments aimed at radiolabeling diaminobiotin by covalently conjugating its carboxyl terminus to a single amino group of a radiolabeled molecule by using carbodiimide were unsuccessful. These attempts failed due to side reactions of the carboxyl group termini of diaminobiotin molecules with amino groups of other diaminobiotin molecules in spite of the use of citraconic anhydride to reversibly block diaminobiotin primary amines.

On the other hand, several attempts at radiolabeling NHS-iminobiotin with a variety of compounds were specific and highly effective, with an efficiency greater than 95% in all cases, as judged by measuring the amount of the unconjugated radiolabeled molecule. Despite the high efficiency of conjugation, it was necessary to devise a purification procedure to separate radiolabeled 2-iminobiotin from unmodified unlabeled 2-iminobiotin to obtain a single-species product. We expected that modification of the carboxyl terminus of 2-iminobiotin would yield a product with a different association constant for streptavidin than that between 2-iminobiotin and streptavidin.

Unlabeled amino acids (methionine, valine, alanine, isoleucine, leucine, cystine, and glycine) were coupled to NHS-2-iminobiotin through their primary amine to test which amino acid allowed a better separation from the unreacted materials by thin layer chromatography (TLC). Since glycine was the most promising of these molecules, we attempted to make a conjugate between iminobiotin and radiolabeled glycine, and then purify it from the unreacted materials. NHS-iminobiotin was detected using a solution containing 2 ml of 5% sodium nitroprusside, 1 ml of 10% sodium hydroxide, 5 ml of 3% hydrogen peroxide, and 15 ml of water (65). This solution yielded purple spots due to its chemical reaction with 2-iminobiotin. Unreacted glycine was detected with ninhydrin (Sigma), which reacts with primary amines and produces orange spots. However, detection of iminobiotin-glycine with the above nitroprusside solution was not as efficient as the detection of unreacted NHS-iminobiotin.

Initial radiolabeling of NHS-iminobiotin was accomplished using $^{14}$C-glycine (98 mCi/mmol; Amersham) with a 50 to 1 molar ratio of NHS-2-iminobiotin to glycine. We attempted an initial purification using TLC on silica gel 60 F254 plates (EM Separations Technologies) with a running solution containing 9:1:1 vol/vol/vol ratio of chloroform:methanol:acetic acid. This solution enabled efficient separation of 2-iminobiotin-glycine from unreacted glycine. However, the separation of 2-iminobiotin-glycine from unreacted 2-iminobiotin was small and was complicated due to the use of the organic solvent dimethylsulfoxide (DMSO) required to dissolve NHS-iminobiotin. DMSO diffused the materials loaded onto the silica plate and made the distinction of products from reactants more difficult. To improve the resolution, the concentration of DMSO and NHS-iminobiotin were reduced to concentrate 2-iminobiotin-glycine to a small region. In this manner, it was possible to minimize contamination with unreacted 2-iminobiotin, but in return the amount of purified 2-iminobiotin-glycine was reduced significantly.

We also attempted to obtain a radiolabeled 2-iminobiotin molecule using [1-$^3$H]Ethan-1-ol-2-amine hydrochloride (29 Ci/mmol; Amersham) with a 50 to 1 molar ratio of NHS-2-iminobiotin to ethanolamine. The solution used to separate 2-iminobiotin-ethanolamine from 2-iminobiotin was 40:20:20 vol/vol/vol ratio of sec-butanol:acetic acid:water. The detection of the radiolabeled molecule was readily accomplished; however, 2-iminobiotin-ethanolamine was contaminated with unreacted 2-iminobiotin; and again, the radiolabeled complex was not useful for our applications.

All procedures aimed at purifying radiolabeled 2-iminobiotin from unreacted 2-iminobiotin by TLC were unsuccessful. Therefore an alternative purification procedure was developed to minimize the large molar excess of unreacted 2-iminobiotin prior to its conjugation to a radiolabeled molecule. This was accomplished by immobilizing cystamine, a disulfide containing material, through one of its amines to NHS-activated sepharose, and NHS-2-iminobiotin to the remaining available amine of cystamine. In this manner, non-immobilized NHS-2-iminobiotin molecules were removed, leaving 2-iminobiotin connected to the sepharose matrix through the cleavable cystamine linker. Cysteamine-2-iminobiotin molecules were released with a reducing agent and coupled through the sulfhydryl group of cysteamine to $^{14}$C-iodoacetamide.

This 2-iminobiotin immobilization procedure was required to obtain a single-species molecule and avoid complications derived from the competition between 2-iminobiotin and 2-iminobiotin-cysteamine-acetamide for the streptavidin biotin-binding site. Although it is expected that 2-iminobiotin-cysteamine-acetamide would have a lower association constant for streptavidin than 2-iminobiotin because the former cannot make hydrogen bonds with Asn-49 and Ser-88 due to its unmodified carboxyl group and the latter can, contamination of 2-iminobiotin-cysteamine-iodoacetamide with 2-iminobiotin may lead to errors in the determination of association constants.

Labeling efficiency of 2-iminobiotin-cysteamine with $^{14}$C-iodoacetamide ranged between 70–80%, as estimated by measuring the amount of radiolabeled 2-iminobiotin bound to a known amount of streptavidin measured by 14C-biotin. This indicated that not all modified 2-iminobiotin-cysteamine molecules were radiolabeled, probably because of the formation of 2-iminobiotin-cysteamine dimers through the sulfhydryl group of cysteamine. To obtain a single-species molecule, DTT was added to reduce disulfides followed by the addition of unlabeled iodoacetamide. Unreacted iodoacetamide was removed by purifying 2-iminobiotin-cysteamine-acetamide molecules through a streptavidin column.

To test for the purity of the final product, modified 2-iminobiotin molecules were incubated in a molar ratio of 1.5, 2, and 3 to natural core streptavidin. It was observed that regardless of the excess of 2-iminobiotin-cysteamine-acetamide, the same amount of radiolabeled material remained bound. This indicated that the purified mixture consisted of a single species of radiolabeled and non-radiolabeled iminobiotin-cysteamine-acetamide molecules or that the concentration of unmodified 2-iminobiotin in the purified 2-iminobiotin-cysteamine-acetamide solution was too low to be detected.

In addition to this procedure, we developed another protocol using reversed-phase chromatography on an FPLC system that allowed us to obtain $^{14}$C- or $^3$H-labeled 2-iminobiotin material, that was used to determine association constants between streptavidin and biotin derivatives. Again, several amino acids (tryptophan, tyrosine, leucine, isoleucine, methionine, aspartic acid, serine and glycine) were used to conjugate their amino groups with NHS-iminobiotin. Experimental results showed that there was a good separation of 2-iminobiotin-tryptophan from 2-iminobiotin and tryptophan. However, this complex decomposed under the acidic conditions used during the purification procedure, and in addition bound non-specifically to the filtration membrane used for the determination of association constants.

On the other hand, iminobiotin-glycine was stable under acidic conditions, did not interact with the filtration membrane, and could be purified with a reversed-phase column. No polar organic solvent was necessary to elute the product during the purification procedure. It was observed that as soon as DMF was removed by washing the column with a phosphate buffer, 2-iminobiotin-glycine readily eluted followed by 2-iminobiotin and unreacted NHS-iminobiotin. The quality of the purified 2-iminobiotin-glycine complex was determined by measuring the binding ability of an identical amount of streptavidin separately with $^{14}$C-biotin and 2-iminobiotin-$^{14}$C-glycine. The sample with 2-iminobiotin-$^{14}$C-glycine yielded an amount that was between 1% and 2% lower than that measured with $^{14}$C-biotin. This experiment was repeated with twice the amount of 2-iminobiotin-$^{14}$C-glycine with similar results. This led us to the conclusion that the purity of 2-iminobiotin-$^{14}$C-glycine was at least 98%. The radiochemical purity of this product was obtained by incubating 2-iminobiotin-$^{14}$C-glycine in the presence of a ten-fold molar excess of natural core streptavidin. The amount of free label ranged between 1.1% and 0.7%.

4. Association constants

Streptavidin constructs with a very low affinity for biotin were obtained by introducing two amino acid substitutions within the streptavidin biotin-binding site. The association constants between Stv-A23D27 and biotin and that between Stv-A23E27 and biotin were measured at (1.4 0.2)×10$^4$ M-1, and (1.4 0.2)×10$^5$ M-1, respectively. It was expected that Stv-A23E27, which contains Glu at residue 27, would have a lower association constant for biotin than Stv-A23D27, which has Asp at that residue, because the longer side chain of Glu would not only cause electrostatic repulsion with the ureido oxygen of biotin but as well as sterically hinder biotin. It is believed that the higher association constant of Stv-A23E27 for biotin is primarily due to electrostatic repulsion differences between the side chains of Asp-27 and Glu-27 with Asp-128. Based on these assumptions, the results suggest that probably biotin binds to Stv-A23E27 more strongly than to Stv-A23D27 to minimize the higher repulsion between Glu-27 and Asp-128 than that between Asp-27 and Asp-128.

The association constants between Stv-A23D27 and 2-iminobiotin-$^{14}$C-glycine and Stv-A23E27 and 2-iminobiotin-$^{14}$C-glycine were estimated at (3.2 0.2)×10$^5$ M-1 and (3.1 0.2)×10$^5$ M-1, respectively. These measurements were useful to determine the association constants between unmodified 2-iminobiotin and diaminobiotin and these streptavidins by competition assays with the aid of 2-iminobiotin-$^{14}$C-glycine. The association constant between Stv-A23D27 and 2-iminobiotin was measured at $(1.0\pm0.1)\times10^6$ M$^{-1}$ which is approximately three times higher than that between Stv-A23D27 and 2-iminobiotin-$^{14}$C-glycine. However, Stv-A23E27 had an association constant of $(1.2\pm0.2)\times10^5$ M$^{-1}$, which is approximately two and a half times smaller than that between Stv-A23E27 and 2-iminobiotin-14C-glycine. Further analysis of these results show that there is a second binding site in these streptavidin constructs. The association constants at this new site between Stv-A23D27 and 2-iminobiotin-$^{14}$C-glycine and Stv-A23E27 and 2-iminobiotin-14C-glycine are $(5.1\pm1.9)\times10^4$ M-1 and $(6.0\pm1.2)\times10^4$ M$^{-1}$, respectively.

Diaminobiotin bound both streptavidin constructs with lower affinity than 2-$^{14}$C-iminobiotin-glycine. The association constant between Stv-A23D27 and diaminobiotin was measured at $(2.7\pm0.3)\times10^4$ M$^{-1}$. It was difficult to accurately measure the association constant between Stv-A23E27 and diaminobiotin because of a significant affinity difference between 2-iminobiotin-$^{14}$C-glycine and diaminobiotin. From the data collected, we estimate an upper limit for this association constant of $5\times10^3$ M$^{-1}$.

Despite the association constant between Stv-A23E27 and diaminobiotin is very low, we were still able to purify to homogeneity Stv-A23E27 by affinity chromatography using diaminobiotin-agarose. This result can be explained if one considers that there are four available biotin-binding sites in streptavidin and that it is possible that several immobilized diaminobiotin molecules can bind simultaneously to a single streptavidin tetramer.

From the above, it is clear that the introduction of two amino acid substitutions in residues that interact with the ureido oxygen from biotin are sufficient to destabilize the strong binding between streptavidin and biotin. The substitutions, Ala for Asn-23 and the additional replacement of Asp and Glu for Ser-27, introduced in the streptavidin biotin-binding site, had a dramatic effect in biotin binding leading to a reduction in affinity of at least ten orders of magnitude at pH 7.5.

STv-A23D27 has a very weak affinity for biotin, and an almost 100-fold higher affinity for iminobiotin. On the other hand, Stv-A23E27 binds biotin and 2-iminobiotin with similar affinity. However, Stv-A23E27 binds 2-iminobiotin-glycine with a three-fold higher affinity than unmodified iminobiotin. This is an interesting result that suggests that glycine, covalently to 2-iminobiotin, interacts with streptavidin amino acids.

The above demonstrates that it is possible to adapt the biotin-binding site of streptavidin so that the biotin derivative 2-iminobiotin can bind to this binding site with a higher association constant than biotin. These streptavidin constructs might be useful in experiments using the streptavidin-biotin complex. Since the ability of these constructs to bind biotin has been disabled, these streptavidin constructs could be used to block non-specific binding sites to which natural streptavidin binds without producing a signal after the addition of labeled-biotin. Stv-A23D27 and 2-iminobiotin could also be used in experiments where the presence of biotin precludes the utilization of the streptavidin-biotin system. Finally, because these proteins have a pH dependent affinity for diaminobiotin and their purification requires mild conditions, either Stv-A23D27 or Stv-A23E27 can be used for the purification of diaminobiotinylated molecules.

What is claimed is:

1. An isolated and purified nucleic acid molecule consisting of nucleic acids encoding a streptavidin mutant having a higher affinity for a biotin substitute than for biotin.

2. The nucleic acid molecule of claim 1, wherein said streptavidin mutant has a higher affinity for 2-iminobiotin than for biotin.

3. The nucleic acid molecule of claim 1, wherein said molecule encodes a streptavidin mutant consisting of amino acids 16–133 of the 159-amino acid natural streptavidin (SEQ ID NO: 2), wherein said molecule comprises one or more codon substitutions such that said mutant comprises one or more amino acid substitutions.

4. The nucleic acid molecule of claim 3, wherein the codon for Asn at position 23 of said 159-amino acid natural streptavidin is substituted with a codon for Ala.

5. The nucleic acid molecule of claim 4, wherein the codon for Ser at position 27 of said 159-amino acid natural streptavidin is substituted with a codon for Glu.

6. The nucleic acid molecule of claim 4, wherein the codon for Ser at position 27 of said 159-amino acid natural streptavidin is substituted with a codon for Asp.

7. An isolated and purified nucleic acid molecule consisting of nucleic acid encoding a streptavidin mutant consisting of amino acids 16–133 of the 159-amino acid natural streptavidin (SEQ ID NO: 2), wherein said molecule comprises one or more codon substitutions such that said mutant comprises one or more amino acid substitutions and has a higher affinity for a biotin substitute than for biotin.

8. The nucleic acid molecule of claim 7, wherein said streptavidin mutant has a higher affinity for 2-iminobiotin than for biotin.

9. The nucleic acid molecule of claim 8, wherein the codon for Asn at position 23 of said 159-amino acid natural streptavidin is substituted with a codon for Ala.

10. The nucleic acid molecule of claim 9, wherein the codon for Ser at position 27 of said 159-amino acid natural streptavidin is substituted with a codon for Glu.

11. The nucleic acid molecule of claim 9, wherein the codon for Ser at position 27 of said 159-amino acid natural streptavidin is substituted with a codon for Asp.

12. A streptavidin mutant having a higher affinity for a biotin substitute than for biotin.

13. The streptavidin mutant of claim 12, wherein said mutant has a higher affinity for 2-iminobiotin than for biotin.

14. The streptavidin mutant of claim 13, consisting of amino acids 16 to 133 of the 159-amino acid natural streptavidin (SEQ ID NO:2), wherein said mutant comprises one or more amino acid substitutions.

15. The streptavidin mutant of claim 14, wherein Asn at position 23 of said 159-amino acid natural streptavidin is substituted with Ala.

16. The streptavidin mutant of claim 15, wherein Ser at position 27 of said 159-amino acid natural streptavidin is substituted with Glu.

17. The streptavidin mutant of claim 15, wherein Ser at position 27 of said 159-amino acid natural streptavidin is substituted with Asp.

18. A streptavidin mutant consisting of amino acids 16 to 133 of the 159-amino acid natural streptavidin (SEQ ID NO:2), wherein said mutant comprises one or more amino acid substitutions and has a higher affinity for 2-iminobiotin than for biotin.

19. The streptavidin mutant of claim 18, wherein Asn at position 23 of said 159-amino acid natural streptavidin is substituted with Ala.

20. The streptavidin mutant of claim 19, wherein Ser at position 27 of said 159-amino acid natural streptavidin is substituted with Glu.

21. The streptavidin mutant of claim 19, wherein Ser at position 27 of said 159-amino acid natural streptavidin is substituted with Asp.

* * * * *